United States Patent [19]

Epstein et al.

[11] Patent Number: 5,509,927
[45] Date of Patent: *Apr. 23, 1996

[54] PROGRAMMING SYSTEM HAVING MEANS FOR RECORDING AND ANALYZING A PATIENT'S CARDIAC SIGNAL

[75] Inventors: Andrew E. Epstein, Birmingham, Ala.; James L. Duncan, Alpharetta, Ga.; Paul A. Levine, Santa Clarita; Jason A. Sholder, Beverly Hills, both of Calif.

[73] Assignee: Pacesetter, Inc., Sylmar, Calif.

[*] Notice: The term of this patent shall not extend beyond the expiration date of Pat. No. 5,421,830.

[21] Appl. No.: 381,799

[22] Filed: Feb. 1, 1995

Related U.S. Application Data

[63] Continuation of Ser. No. 113,540, Aug. 27, 1993, Pat. No. 5,421,830.

[51] Int. Cl.$^6$ .................................................. A61N 1/37
[52] U.S. Cl. ........................................................ 607/32
[58] Field of Search ................................. 607/27, 30, 32, 607/60, 18, 17, 9, 5; 128/903

[56] References Cited

U.S. PATENT DOCUMENTS

| | | | |
|---|---|---|---|
| 4,146,029 | 3/1979 | Ellinwood, Jr. | 128/903 |
| 4,193,393 | 3/1980 | Schlager | 128/710 |
| 4,223,678 | 9/1980 | Langer et al. | 607/5 |
| 4,476,869 | 10/1984 | Bihn | 128/419 PT |
| 4,625,730 | 12/1986 | Fountain et al. | 607/27 |
| 4,809,697 | 3/1989 | Causey, III et al. | 128/419 PT |
| 4,969,467 | 11/1990 | Callaghan et al. | 607/30 |
| 5,088,491 | 2/1992 | Schaldach | 607/18 |
| 5,158,078 | 10/1992 | Bennett et al. | 607/27 |
| 5,300,093 | 4/1994 | Koestner et al. | 607/32 |

*Primary Examiner*—George Manuel
*Attorney, Agent, or Firm*—Harold C. Schloss

[57] ABSTRACT

A programming system is provided that allows a physician or medical personnel to optimize the settings of various arrhythmia detection criteria and/or parameters related to hemodynamic performance to be programmed into the implanted cardiac stimulating device. The cardiac stimulating device may be a pacemaker or cardioverter/defibrillator that detects heart arrhythmias by using various arrhythmia detection criteria. The cardiac stimulating device is capable of recording the patient's cardiac signals and/or sensor data. The programming system may play back the recorded signals to test the detection criteria and hemodynamic performance and may simulate the response of the device to the cardiac signal. Alternatively, the programming system may play back an artificially created or previously stored cardiac signal for test purposes. As a result, the recorded signal may be played back repeatedly without unnecessarily stressing the patient's heart. Additionally, the programmer may suggest specific arrhythmia detection criteria and therapies to a physician based on an analysis of a patient's arrhythmia.

8 Claims, 4 Drawing Sheets pages.

PROGRAMMING SYSTEM HAVING MEANS FOR RECORDING AND ANALYZING A PATIENT'S CARDIAC SIGNAL

CROSS-REFERENCE TO RELATED APPLICATIONS

This is a continuation of application Ser. No. 08/113,540, filed Aug. 27, 1993 now U.S. Pat. No. 5,421,830.

FIELD OF THE INVENTION

This invention relates to programing systems for implantable medical devices, and particularly, to microprocessor-based programmers for implantable cardiac stimulating devices.

BACKGROUND OF THE INVENTION

It has recently become possible to provide patients with implantable cardiac stimulating devices that detect various cardiac arrhythmias and respond by applying therapies, such as a series of electrical pacing pulses or a cardioversion or defibrillation shock, to a patient's heart. The sophistication of the device to be implanted in a particular patient depends to a large degree on the type of cardiac arrhythmia that patient has. For instance, if a patient suffers from bradycardia, a standard fixed-rate or rate-responsive pacemaker may be sufficient. If, however, a patient suffers from episodes of tachycardia, which may in turn lead to fibrillation, a more complex device such as an implantable cardioverter and/or defibrillator may be warranted. Typically, cardiac stimulating devices such as these can respond to different detected arrhythmias with varying levels of therapy. For instance, if an episode of tachycardia is detected, the device can apply a series of antitachycardia pulses to the heart. If, however, tachycardia persists, even after applying antitachycardia pulses, an appropriate response might be to apply a cardioversion shock.

Because the level of therapy applied to the heart depends on the type of arrhythmia a patient experiences, it is important for a cardiac stimulating device to use appropriate detection criteria to classify and confirm a patient's arrhythmia. For example, tachycardias can be classified into zones, each having a different threshold heartbeat rate. When a threshold has been exceeded for a predetermined period, the cardiac stimulating device confirms tachycardia and responds by applying antitachycardia therapy to the patient. By setting the thresholds correctly, the optimum response of the cardiac stimulating device to such an arrhythmia can be ensured. Further, within each zone a series of applicable therapies may be applied in an effort to terminate an arrhythmia episode. The detection thresholds and the therapies to be applied to the patient's heart can be individually programmed into a cardiac stimulating device by a physician, who uses a "programmer" which is typically microprocessor-based.

The programer provides a user-friendly interface, such as a touch screen, with which a user can set the desired values of various adjustable parameters for the cardiac stimulating device. After the selected values of these parameters are input into the programmer by the user, the programmer transmits this data to the cardiac stimulating device via a telemetry head.

Each patient has a different cardiac condition, so it is advantageous for the physician to adjust the programmable parameters to maximize the performance of the cardiac stimulating device for each individual. It may be beneficial if a physician adjusts the detection criteria to be more sensitive, so that arrhythmias are confirmed more quickly and the appropriate therapy is applied as soon as possible. Also, the response of the device following arrhythmia detection can be controlled. For example, the most aggressive therapies, such as the application of a cardioversion shock, may only be applied after less aggressive therapies have been unsuccessfully used, although such a shock should always be applied to the patient early enough to avoid subjecting the patient to unnecessary danger associated with persistence of the abnormal rhythm.

A physician traditionally optimizes the antitachycardia settings of a cardiac stimulating device by inducing tachycardia in an anesthetized or sedated patient. The behavior of the device, which is surgically implanted in the patient, to the induced tachycardia is then observed to determine if the detection criteria that were selected are effective at confirming tachycardia and if the therapy that is applied is effective in ending the tachycardia episode.

However, inducing tachycardia an excessive number of times could be stressful to the patient's heart, so the physician can only use this procedure a limited number of times. Further, if the patient has an arrhythmia episode that is recorded "in the field," it would be beneficial if the physician could test various detection criteria using that recorded cardiac signal, because a cardiac signal captured in the field may more accurately reflect the patient's typical arrhythmias than the cardiac signal produced when tachycardia is induced in a patient. If the programmer could generate the patient's cardiac signal, the physician could optimize the selection of detection criteria without having to repeatedly induce the tachycardia in the patient. With a sufficiently sophisticated programming system, a programmer could recommend appropriate detection criteria and levels of therapy to a physician based on a recording of a patient's intrinsic cardiac signal taken during an arrhythmia episode. Further, if the performance of the cardiac stimulating device could be simulated, optimization could be performed more quickly than if the cardiac stimulating device's response to the cardiac signal had to be telemetered from the device following a detected episode.

SUMMARY OF THE INVENTION

According to the principles of the present invention, a programming system is provided that can play back a recorded segment of a patient's cardiac signal so that the settings of the implanted device may be adjusted to optimize device performance.

As used herein, a "cardiac signal" includes a single intracardiac depolarization waveform (e.g., a P-wave, an R-wave, etc.) and/or a continuous series of depolarization waveforms, each waveform having a specific beat-to-beat cycle length and, potentially, varying morphology. The recurring pattern of a series of depolarization waveforms is also known as a "cardiac rhythm". An "electrogram" is the recording of a signal using electrodes directly on the tissue, rather than at the surface of the body. Thus, an "intracardiac electrogram" refers to a recording of cardiac signals occurring within the heart using electrodes in direct contact with the heart (e.g., with endocardial leads placed transvenously within the heart or epicardial leads placed on the external surface of the heart).

For purposes of this invention, either the continuous intracardiac electrogram may be digitized, stored and analyzed, or the intracardiac electrogram may be compressed to store, as a minimum, a set of heartbeat intervals (e.g., the P-P intervals, R-R intervals, etc.). The programming system of the present invention can make use of the heartbeat intervals, as well as the complete intracardiac electrogram, because knowledge of the heartbeat intervals allows detection of various heart arrhythmias and fibrillation. Whether the complete intracardiac electrogram is used, or only a set of heartbeat intervals, will vary depending on the type of cardiac stimulating device and its available memory capacity.

In one embodiment, the physician may acquire the cardiac signal by inducing a single episode of tachycardia in a patient, so that the pulse generator can then record the patient's intracardiac electrogram and telemeter it to the programmer device for analysis.

Alternatively, the implanted cardiac stimulating device can record the patient's intracardiac electrogram when the patient is in the field. Recording in the field will often produce cardiac signals that are more representative of a patient's usual arrhythmia than the signals obtained by artificial induction.

Once the signal is recorded, the signals are telemetered to, or otherwise received by, the programmer. The programmer can then repetitively replay the recorded cardiac signals so that the values of the detection criteria can be optimized, Parameters that need to be adjusted include, but are not limited to: rate, rate stability, sudden onset delta, probability density function, morphology detection, slew rate, a specific number of intervals (arrhythmia duration), signal amplitudes, frequency content and activation sequence. When successful detection criteria have been optimized, the patient's implanted cardiac stimulating device can be reprogrammed accordingly.

In the preferred embodiment, the programmer is used to simulate the detection response of the implanted device. By simulating the response of the device, it is possible to arrive at an optimum set of detection criteria very quickly. In fact, the programmer may include the logic necessary to analyze the patient's recorded signals and suggest specific detection criteria and therapies to the physician. The physician can then program the cardiac stimulating device with the recommended settings.

In an alternate embodiment, an external device may be used to simulate the detection response of the implanted device. In this case, the programmer would be used to replay the recorded signal to the external device while the values of the detection criteria parameters in the external device are changed until the performance was optimized. The physician can then program the implanted device with the same values as the external device.

In yet another embodiment, the physician has the option to artificially generate a "test" signal in the programmer to simulate several expected types of arrhythmias. For example, the physician could select the rate of the test signal, the degree of variability of the test signal, the signal morphology and the signal amplitude based on previous measurements or Holter monitoring. As described above, the physician would then optimize the detection criteria to determine appropriate settings.

In one embodiment, the entire arrhythmia episode is recorded and analyzed. In another embodiment, the individual cardiac signals and the cycle length can be recorded and analyzed. The latter embodiment has the advantage of using much less memory to store the full arrhythmia episode.

Advantageously, the recorded segment may be played back repeatedly without the need to induce arrhythmias in the patient. Thus, the device's detection criteria and the therapies to be applied by the implanted device can be optimized without stressing the patient's heart unnecessarily.

In another embodiment, it may be desirable to record other physiologic sensors to determine a patient's physical condition. For example, by recording a sensor signal concurrent with the cardiac signal, one can determine whether the cardiac signal is physiologic or pathologic. This can be of significant value in optimizing the performance of the implanted device, both for arrhythmia detection and for rate-response detection. More specifically, if a cardiac stimulating device is provided with a motion sensor to determine a patient's exercise level, motion-related information can be recorded and analyzed by the programmer to optimize the rate-response parameters, e.g., rate threshold, slope, minimum rate, maximum rate, gain, reaction time, and recovery time, etc.

Therefore, according to the present invention, a programming system is provided for optimizing the performance of an implanted cardiac stimulating device. The programming system replays cardiac signals and/or sensor data and analyzes and optimizes performance parameters, allowing adjustment of the device response without repeatedly inducing the original condition (i.e., a tachyarrhythmia or exercise). The implanted cardiac stimulating device can then be reprogrammed to the optimum parameters and apply corresponding therapies to a patient's heart.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENT

Figure 1:
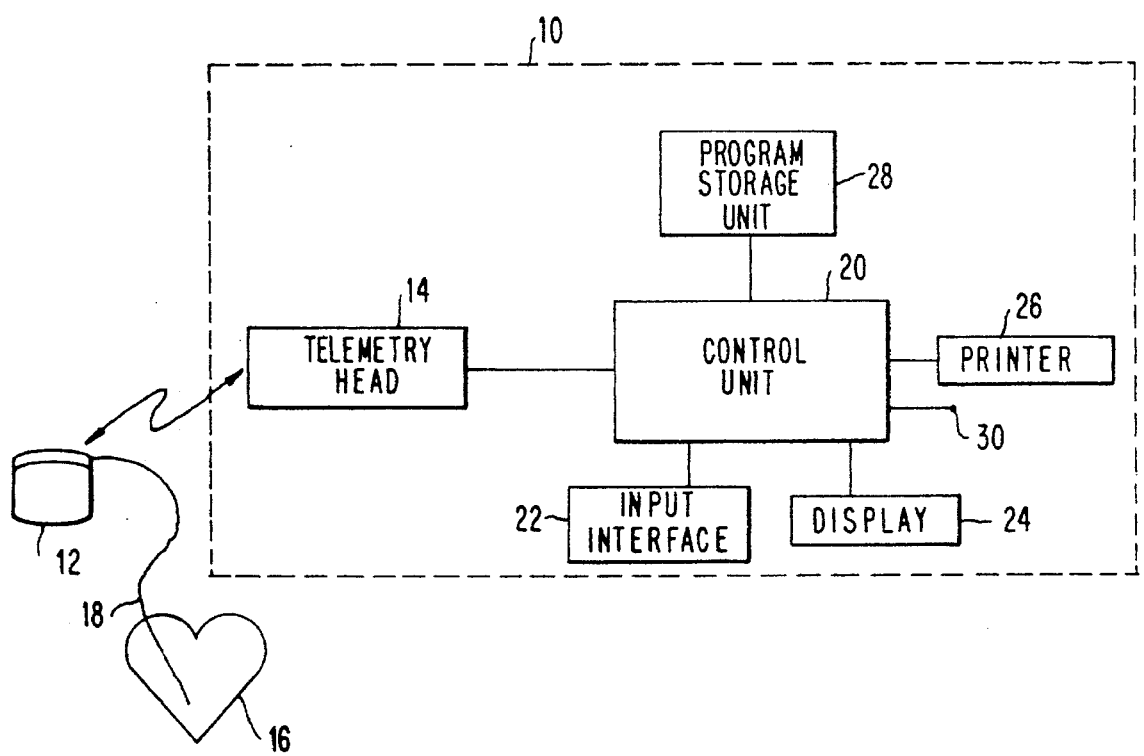
FIG. 1 is a schematic diagram of an illustrative programming system for a cardiac stimulating device in accordance with the principles of the invention.

A physician or medical technician may use a programing unit called a "programmer" to program the detection criteria into a programmable cardiac stimulating device. As shown in FIG. 1, a programming system according to the present invention incorporates a programmer 10, which is linked to a cardiac stimulating device 12 via telemetry head 14. The cardiac stimulating device 12 is attached to the patient's heart 16 with a lead 18. (Although only one lead is shown in FIG. 1, it is understood that more leads may be present, such as, a two-lead system, e.g., one in the atrium and one in the ventricle.) A control unit 20 is preferably at least partly microprocessor-based, although preferably the control unit 20 is also partly implemented using random logic. An input interface 22 is used by a physician or medical technician to enter commands into the programmer 10. The input interface 22 could be a keyboard, a touch-sensitive pad, a screen with a light pen, or any suitable interface to allow the user to communicate with the control unit 20. Messages and data can be displayed on a display 24 and printed on a printer 26. Programs to control programmer 10 can be supplied using one or more program storage units 28, which could be a read-only memory cartridge, an optical disk drive, a hard disk drive, a floppy disk drive, a tape drive, or any suitable data storage device. Preferably, the programmer 10 has at least one program storage unit 28 for storing data signals derived from the patient's intracardiac electrogram. If desired, data signals may also be sent to an auxiliary display such as an X-Y plotter via a data output terminal 30.

Figure 2:
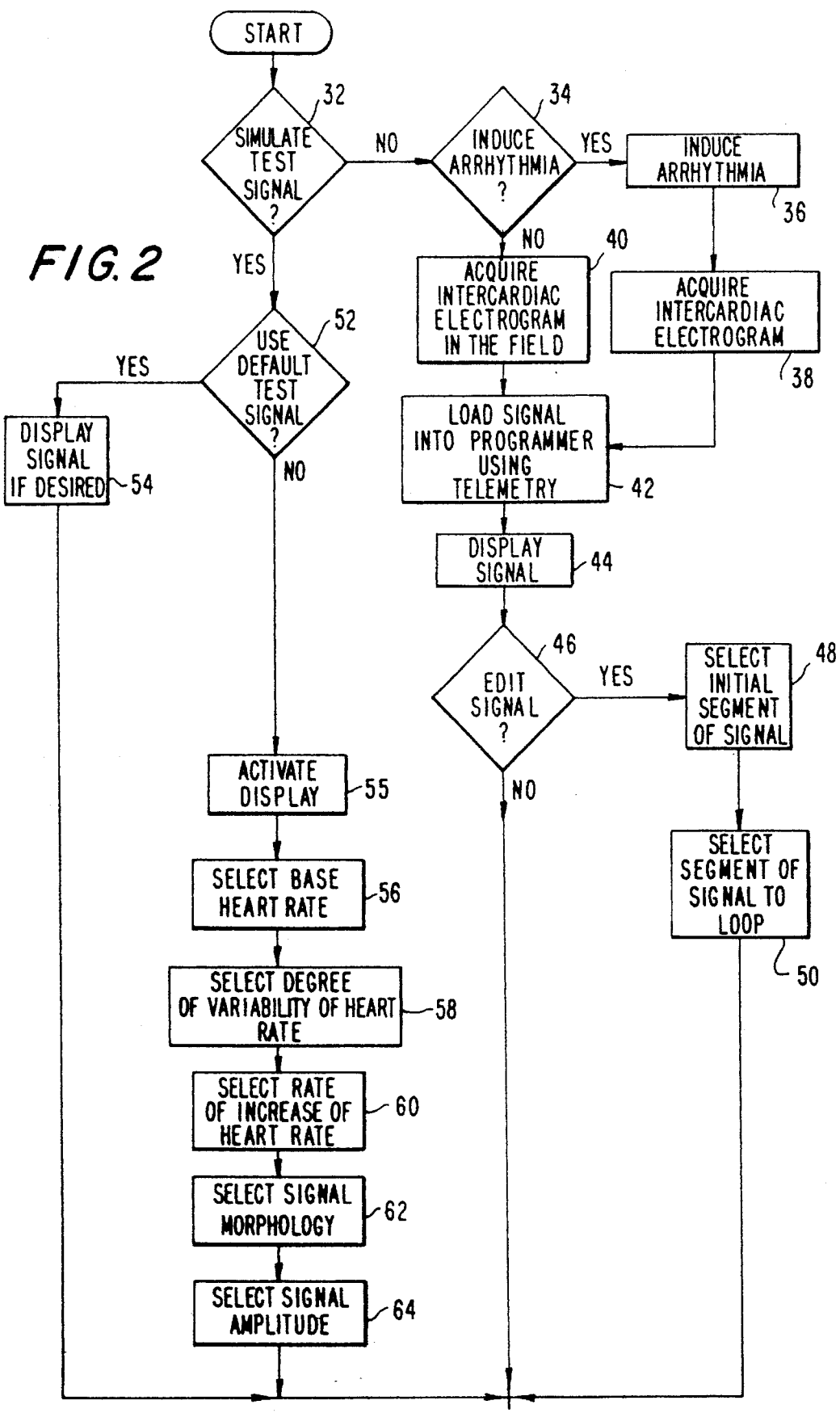
FIGS. 2 and 3 are schematic flowcharts depicting the structure and operation of the programming system is accordance with the principles of the invention.
Figure 3:
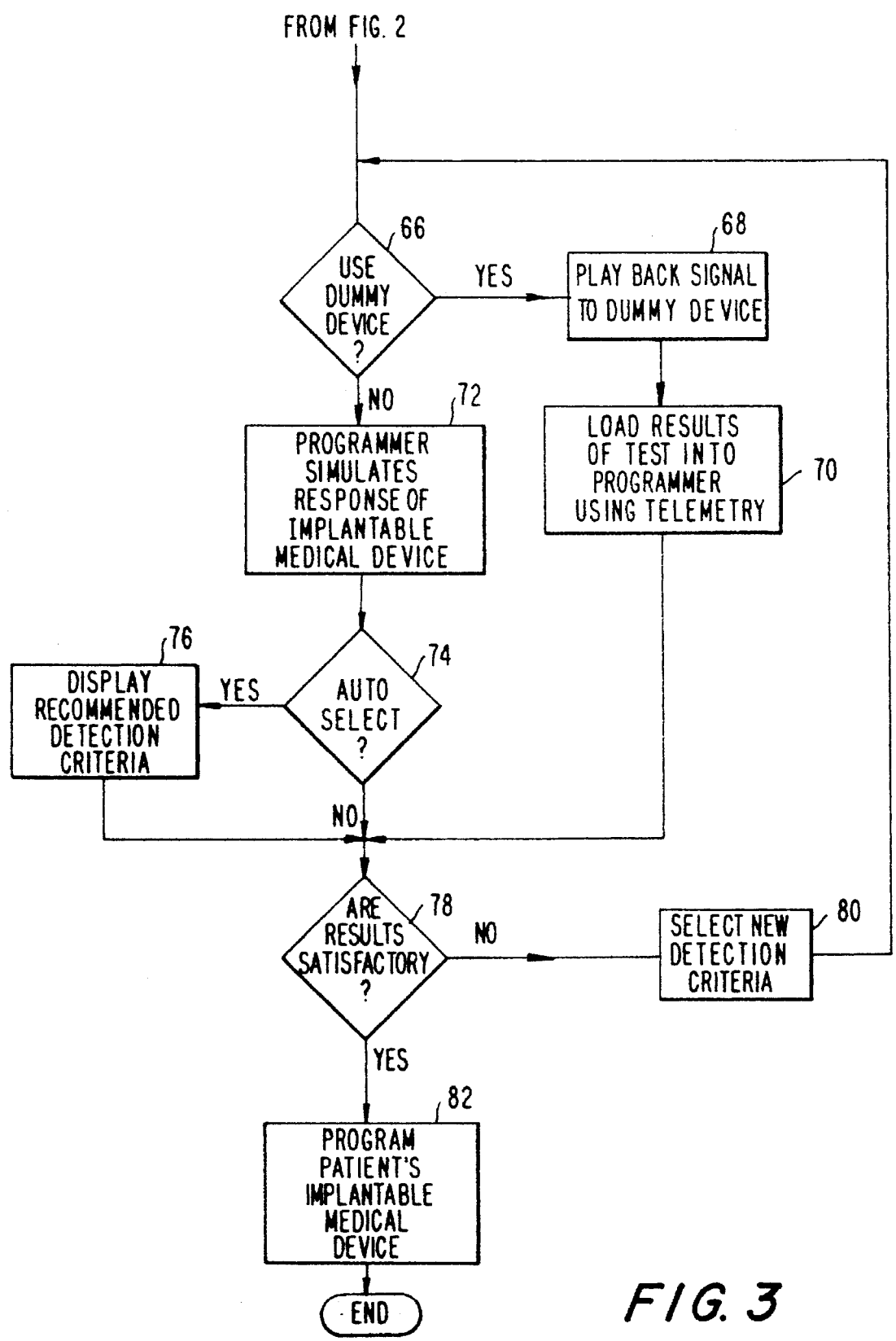

The operation of a computer program for controlling the programming system of the present invention is shown schematically in FIGS. 2 and 3. In operation, the computer program will cause the programming system to display prompts to the user on the display 24, and receive commands from the user via the input interface 22. Initially, at test 32, the programming system prompts the user to decide whether to use the patient's actual cardiac signal or whether the programmer is to simulate the cardiac signal. If, at test 32, the user decides to use the patient's actual cardiac signal, the system next prompts the user to decide if arrhythmia is to be induced in the patient at test 34. If the user responds affirmatively at test 34, the programming system allows the user to induce arrhythmia using any method desired by the user, during step 36. Arrhythmia may be induced by applying an AC voltage to the heart or by applying rapid stimulating pulses. Preferably, fast pulses are used to overpace the patient's heart by first capturing the heartbeat, slowly increasing the heartbeat rate and then applying one or more critically timed pulses. The AC voltage and the fast pulses can be applied directly by the user, or the user can direct the programmer to instruct the cardiac stimulating device that is surgically implanted in the patient to apply the appropriate pulses.

The patient's cardiac signal is recorded by the cardiac stimulating device at step 38, until the user terminates data acquisition or until a predetermined length of time is exceeded. Of course, the implanted cardiac stimulating device is allowed to terminate the arrhythmia episode. Alternatively, the programmer may be used to record and terminate the arrhythmia. If necessary, conventional, non-implanted cardiac stimulating devices can also be used to terminate the arrhythmia.

If, at test 34, the user had decided not to induce arrhythmia, the cardiac signal can be recorded when the patient is "in the field" (step 40). For example, after the cardiac stimulating device confirms an arrhythmia episode, the cardiac signal can be recorded for the period prior to confirmation and during the episode. Whether the complete digitized intracardiac electrogram is stored, or only a set of heartbeat intervals is stored will vary depending on what type of cardiac stimulating device is used and its available memory capacity. As mentioned above, the term "cardiac signal" refers to either a continuous intracardiac electrogram or digitized data representing the lengths of the intervals between successive heartbeats. The programming system of the present invention can make use of the heartbeat intervals, as well as the complete intracardiac electrogram, because knowledge of the heartbeat intervals allows detection of various heart arrhythmias and fibrillation. For example, tachycardia may be confirmed when a patient's heartbeat intervals are too short for several consecutive beats.

If there is sufficient storage capacity in the cardiac stimulating device both the intracardiac electrogram and the corresponding heartbeat intervals can be stored, along with "markers" which indicate, for example, whether an arrhythmia episode has been detected. Further, other physiologic signals measured by the cardiac stimulating device that are indicative of a patient's physical condition can be stored. For example, signals indicative of cardiac contractile activity or hemodynamics could be stored.

Regardless of whether an arrhythmia episode was induced or whether the patient was in the field when the cardiac signal was stored, at step 42 the cardiac signal is transmitted from the cardiac stimulating device 12 to the programmer 10 using telemetry. In order to present the user with an easily recognizable data display format, at step 44 the intracardiac electrogram is displayed on the display 24. If only heartbeat intervals were stored, a graphical representation of, for example, a QRS complex can be displayed at each interval.

After viewing the cardiac signal, the user decides at test 46 whether the signal should be edited. If the user decides to edit the signal, the user may select an initial segment of the recorded signal at step 48. For example, if the recorded cardiac signal is long, the early portion of the signal may only contain a record of the patient's normal sinus rhythm. If desired, the user can remove that portion of the signal, so that the overall testing period will proceed more quickly. At step 50 the user may select a segment of the recorded signal to loop, allowing continuous playback. The user would most likely pick a segment that begins where the initial segment ends, so that the two portions of the recorded signal will match smoothly. He may also wish to cut off the tail of the recorded signal. For instance, if the cardiac stimulating device responded to a confirmed arrhythmia while the signal was being recorded, the stored signal might include the pulses applied during therapy, as well as the cardiac signal. The physician or medical technician may want to eliminate that portion of the recorded cardiac signal so that a clean signal is played back. Further, if the user is attempting to shorten the time required to confirm arrhythmia episodes, it is not necessary to play back portions of the signal subsequent to the point at which the present detection criteria have already led to arrhythmia confirmation. If the recorded cardiac signal is sufficiently long, or if it is desired to test various detection criteria by playing back the recorded signal in its entirety, then the user can decide at test 46 to forego editing.

If, at test 32, the user decided not to use the patient's actual cardiac signal, then the user decides at test 52 if the programming system will use a default cardiac test signal. If a default cardiac test signal is used, it may be displayed, if desired by the user, at step 54. One of several default signals can be used to test the effectiveness of various detection criteria. For instance, average arrhythmia signals, compiled from arrhythmia segments recorded in patients who have experienced the most common types of arrhythmia, may be selected. Additionally, a library of recorded cardiac test signals from various patients may be provided. Although not a simulated signal, a patient's previously recorded cardiac signal may also be used at this point.

If it is desired to simulate a cardiac signal based on user-selected parameters rather than with a default cardiac test signal, the display can be activated by the user to display the simulated cardiac signals at step 55. A user may then select among various parameters that describe the simulated cardiac signal during steps 56, 58, 60, 62 and 64 (not necessarily in that order). The particular parameters shown in these steps are intended to be representative of the general class of parameters a user may wish to enter and are not limited to just those shown in FIG. 2. Not all of the parameters need to be selected by the user. If desired, the programming system can initially provide nominal settings.

One of the parameters a user can vary is the waveform morphology. In general, the morphology of a cardiac waveform can vary considerably between patients and even in a single patient. At step 62, the user can create a unique waveform morphology from scratch or select a morphology using a predefined template. By varying the morphology of the waveform either a monomorphic arrhythmia (having a single shape) or a polymorphic arrhythmia (having multiple, different shapes) may be simulated. If a polymorphic arrhythmia is simulated, the user can either choose the morphology of each complex separately, or can create a simulated rhythm by repeating a pattern of complexes of various morphologies. The pattern could be a randomly generated group of four or five different complexes. Signal morphology can also be selected to simulate fibrillation. Missing beats may be simulated by inserting null beats into the simulated cardiac signal. Preferably, the signal morphology is chosen by selecting from a group of complexes of varying morphologies displayed on the screen.

If desired, the simulated signal may be displayed prior to a complete specification by the user and may then be updated as the user specifies additional parameters. For example, if the user enters a tachycardia heartbeat rate of 200 beats per minute at step 60, the programmer 10 may then display a signal at that rate using a default signal morphology. When the user selects a different signal morphology at step 2, the programmer 10 updates the display 24.

Regardless of whether the user chose to use a simulated test signal or to use a recorded cardiac signal at test 32, the user decides at test 66 (FIG. 3) whether a programmer or an external cardiac stimulating device is to be used to simulate the response of the implanted cardiac stimulating device and to test the detection criteria. (Alternatively, an implanted cardiac stimulating device can also be used to gauge the efficacy of the selected detection criteria. In that case, the cardiac stimulating device does not stimulate the patient during arrhythmia confirmation, but rather telemeters out to the programmer an indication that the arrhythmia was detected.)

If the external device is selected, the recorded intracardiac electrogram signal is played back into the external device at step 68. The external device is preprogrammed with a set of detection criteria to be tested at step 69. The recorded tachyarrhythmia causes the external device to respond as in the event of a real-time cardiac arrhythmia. The response of the external cardiac pacemaker could be obtained by using real-time telemetry, or by recording it in memory and telemetering the results out. Following the application of the test signal the response of the external device is loaded from memory into programmer 10 using telemetry at step 70. (Alternatively, the results could be acquired by electrically connecting the programmer device directly to the proximal end of the exposed lead.)

Figure 4:
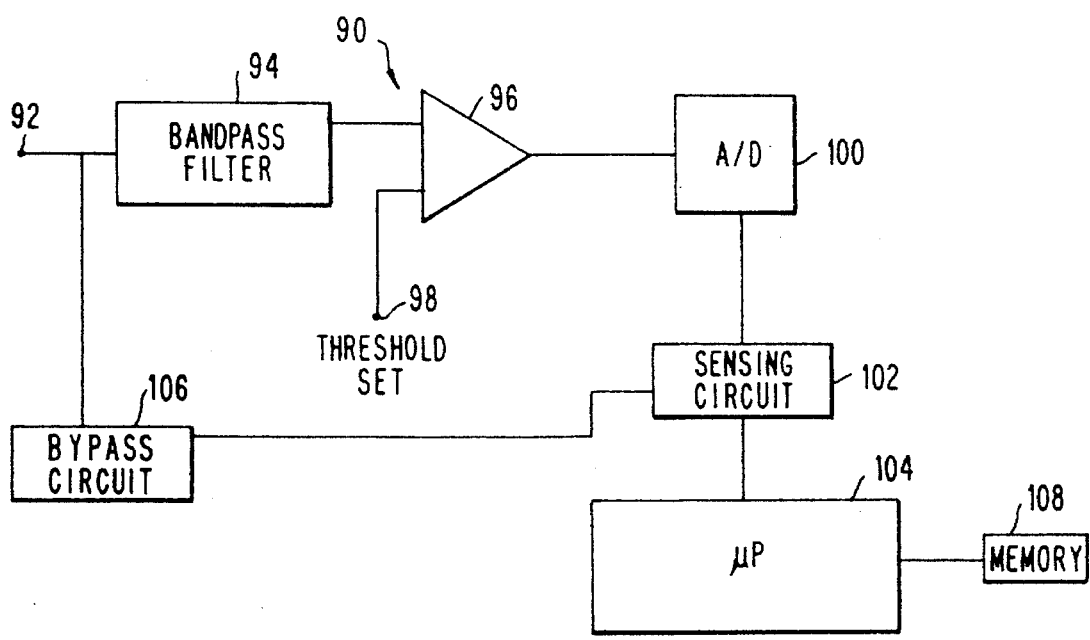
FIG. 4 is a schematic diagram of an illustrative external cardiac stimulating device according to the principles of the invention.

If the complete intracardiac electrogram is provided to the "simulating" device (i.e., either the external device or the programmer), the signal is applied directly to the input lead. As shown in FIG. 4, the simulating device circuitry 90 receives a complete intracardiac electrogram directly from the input lead via input terminal 92. A bandpass filter 94 has low and high frequency rolloffs which simulates the rolloff of the implanted cardiac stimulation device, e.g., approximately 20 and 80 Hz, respectively, although other frequencies are also permitted. A comparator 96 accepts the post-processed signal from the bandpass filter 94 and a threshold set signal at a terminal 98. The comparator 96 outputs those signals that exceed the threshold to an analog-to-digital converter 100. The analog-to-digital converter 100 provides a sensing circuit 102 with a digitized version of the intracardiac electrogram. The sensing circuit 102 then analyzes the digitized signal and extracts the heartbeat intervals and other critical parameters, which it provides to a microprocessor 104.

If the only the heartbeat intervals or digital signals representing the intracardiac electrogram are provided, a different portion of the processing circuitry of the simulating device circuitry 90 must be accessed, i.e., a bypass circuit 106 may be activated after receiving a predefined digital code via the input terminal 92, as shown in FIG. 4. Alternatively, the bypass circuit 106 may be activated by telemetered commands received from programer 10. When activated, the bypass circuit 106 causes the sensing circuit 102 to bypass the analog-to-digital converter 100 and pass the heartbeat intervals present at the input terminal 92 to the microprocessor 104. The microprocessor 104 uses the test detection criteria stored in the memory 108 to determine whether an arrhythmia is present.

In the preferred embodiment, the programmer 10 plays back the cardiac signal internally, at step 72, and simulates the response of the cardiac stimulating device at step 73. As described above, many cardiac stimulating devices are at least partly microprocessor-based. These devices use software modules to implement portions of the algorithms related to confirming the presence of an arrhythmia. The programmer 10 may therefore simulate the operation of a cardiac stimulating device by modeling the control unit in software, taking into account algorithms that are implemented by the microprocessor. Additionally, when the response of a cardiac stimulating device to an intracardiac electrogram test signal is simulated, the effects of the preprocessing circuitry of the particular device are taken into account. For example, the bandpass circuitry, threshold circuitry, and analog-to-digital conversion circuitry can be modeled.

The programming system of the present invention can also analyze the response of the implanted device by adjusting the plurality of detection criteria settings, optimizing for the best performance and display a set of recommend detection criteria settings. For example, if the existing detection criteria cause the device to take too long before applying therapy to a patient, the programming system could recommend a lower rate threshold or a modification of another detection criteria. The programming system may thus automatically recommend a set of detection criteria that will detect certain types of arrhythmia after a fixed period of time, say five seconds. During playback of the cardiac signal, the programming system measures the patient's heart rate as a function of time and calculates the threshold rate that would have caused arrhythmia confirmation within five seconds after initiation of an episode. At test 74, the user determines whether this feature is to be invoked. If it is, the recommended detection criteria are displayed at step 76.

Regardless of whether the auto-analyze feature is used or whether the external device was used, after using the cardiac signal to test a set of detection criteria, the user decides at test 78 if the results are satisfactory. If they are not, new detection criteria are selected at step 80 before returning to test 66. If the results are satisfactory, the successful detection criteria are loaded into the cardiac stimulating device 12 via the telemetry head 14 at step 82.

Although use of the programmer to perform the playback, simulation, and auto-analyze features has been emphasized, a cardiac simulating device could be used to implement the same functions. For example, the cardiac stimulating device could play back a recorded cardiac signal to itself, an external device, or a programmer which simulates the performance of a cardiac stimulating device. The cardiac stimulating device could also simulate a cardiac signal based on default criteria or physician-selected criteria that are received from the programmer. A cardiac stimulating device can also be used to auto-analyze detection criteria based on an analysis of the cardiac arrhythmia.

In another embodiment, it may be desirable to record other physiologic sensors to determine a patient's physical condition. By recording a sensor signal in the field at step 40 (FIG. 2), concurrent with the cardiac signal, the physician can determine whether the cardiac signal is physiologic or pathologic. Recording sensor data can also be of significant value in optimizing the performance of the implanted device, both for arrhythmia detection and for rate-response detection. For example, if a cardiac stimulating device is provided with an activity sensor to determine a patient's exercise level, activity-related information can be recorded and analyzed by the programmer to optimize a plurality of rate-response parameters, e.g., rate threshold, slope, minimum rate, maximum rate, gain, reaction time, and recovery time, etc. Assuming for the moment that the programmer is performing the simulation, both the cardiac signal and the sensor signal would be played back at step 72 and the response of the implanted device would be simulated at step 73. If the auto-analyze function were selected, the system would analyze the signals for optimum rate-response performance and display the recommended settings at step 76. If the physician approved of the results achieved with the recommended settings, they would be reprogrammed into the implanted device at step 82.

Several factors must be considered when deciding whether to implement a particular function in the programmer or the cardiac stimulating device. For example, a cardiac stimulating device has limited battery power, so that using the device's microprocessor and control circuitry extensively shortens battery life. Further, the cost of a cardiac stimulating device is borne by a single patient, whereas the cost of a programmer is shared among many patients.

Thus it is seen that a programming system is provided that allows a physician to optimize the performance of an implanted cardiac stimulating device. The programming system replays cardiac signals and analyzes performance parameters, allowing adjustment of the device response without actually inducing the original condition (i.e., a tachyarrhythmia or exercise). The implanted cardiac stimulating device can then be reprogrammed to the optimum parameters and apply corresponding therapies to a patient's heart. One skilled in the art will appreciate that the present invention can be practiced by other than the described embodiments, which are presented for purposes of illustration and not of limitation, and the present invention is limited only by the claims that follow.

What is claimed is:

1. A programming system for programming and optimizing a plurality of programmed parameters for use in a cardiac stimulating device, the cardiac stimulating device being capable of applying a corresponding therapy to a patient's heart based on the plurality of programmed parameters, the programming system comprising:

means for recording a patient's cardiac signal over a predetermined time interval for playback;

means for playing back such cardiac signal;

first telemetry means for telemetering the recorded cardiac signal; and external programmer means comprising:

second telemetering means for receiving the telemetered recorded cardiac signal; and means for analyzing the response of the cardiac stimulating device to the played back cardiac signal based on the plurality of programmed parameters.

2. The programming system of claim 1, wherein the external programmer means further comprises means for repetitively replaying the recorded cardiac signal and for determining the optimal value for each of the plurality of programmed parameters.

3. The programming system of claim 2, wherein the plurality of programmed parameters includes detection criteria for the cardiac stimulating device and wherein the external programmer means includes means for simulating the detection response of the cardiac stimulating device for optimizing the detection criteria.

4. The programming system of claim 3, further comprising means for reprogramming the cardiac stimulating device with the optimized detection criteria.

5. The programming system of claim 3, wherein the cardiac signal comprises an episode of arrhythmia and the detection criteria comprises arrhythmia detection criteria.

6. The programming system of claim 1, further comprising means for editing the played back cardiac signal.

7. A programming system for programming and optimizing a plurality of programmed parameters comprising arrhythmia detection criteria for use in a cardiac stimulating device, the cardiac stimulating device being capable of applying a corresponding therapy to a patient's heart based upon the arrhythmia detection criteria, the programming system comprising:

means for recording a patient's cardiac signal over a predetermined time interval for playback, the cardiac signal comprising an episode of arrhythmia;

means for playing back such recorded arrhythmia signal;

first telemetry means for telemetering the recorded arrhythmia signal; and external programmer means comprising:

second telemetry means for receiving the telemetered recorded arrhythmia signal; and means for analyzing the response of the cardiac stimulating device to the played back arrhythmia signals based on the arrhythmia detection criteria for optimizing such arrhythmia criteria.

8. The programming system of claim 7, further comprising means for generating a simulated cardiac signal.

* * * * *